United States Patent [19]

Boschan

[11] 4,125,563

[45] Nov. 14, 1978

[54] PROCESS FOR MAKING NITROARYLACETYLENES AND NITROARYLALDEHYDES

[75] Inventor: Robert H. Boschan, Los Angeles, Calif.

[73] Assignee: Hughes Aircraft Company, Culver City, Calif.

[21] Appl. No.: 828,016

[22] Filed: Aug. 26, 1977

Related U.S. Application Data

[62] Division of Ser. No. 347,502, Apr. 3, 1973, abandoned.

[51] Int. Cl.$^2$ ..................... C07C 47/48; C07C 79/10; C07C 79/12
[52] U.S. Cl. ................................. 260/645; 260/599; 260/600 R; 260/646; 568/584; 568/585; 568/630
[58] Field of Search .............. 260/599, 612 D, 613 D, 260/645, 646, 600 R

[56] References Cited

U.S. PATENT DOCUMENTS

| | | | |
|---|---|---|---|
| 3,952,067 | 4/1976 | Douglas et al. | 260/645 X |
| 3,996,289 | 12/1976 | Meyer | 260/599 |

*Primary Examiner*—Leland A. Sebastian
*Attorney, Agent, or Firm*—Booker T. Hogan, Jr.; W. H. MacAllister

[57] ABSTRACT

I have discovered a process for making nitroarylacetylenes and aminoarylacetylenes in which the aryl radical is a phenylene radical or a diphenylene radical. With the exception of p-aminophenylacetylene, the compounds produced by this process are novel. The compounds are all useful as intermediates in the preparation of addition polymers utilizing a polymeric backbone of polyimides. The addition polymers are useful as adhesives and as laminating resins.

5 Claims, No Drawings

PROCESS FOR MAKING NITROARYLACETYLENES AND NITROARYLALDEHYDES

The inventions herein described were made in the course of or under a contract with the United States Air Force.

This is a division of application Ser. No. 347,502, filed Apr. 3, 1973, now abandoned.

RELATED APPLICATIONS

In U.S. Application Ser. No. 347,501, filed concurrently herewith in the names of Norman Bilow, Leroy J. Miller and Abraham Landis entitled, "Acetylene Substituted Polyimide Oligomers" (now issued as U.S. Pat. No. 3,845,018), the compounds produced by the presently claimed process are reacted with anhydrideterminated polyimides. The polyimides are formed by the reaction of an aromatic tetracarboxylate such as benzophenone dianhydride with an aromatic diamino compound such as 4,4'-diamino diphenyl ether. The resultant products are acetylene-substituted polyimide prepolymers that are exceptionally useful as laminating resins and as adhesives.

U.S. Application Ser. No. 828,018, filed concurrently herewith, is a continuation of U.S. Application Ser. No. 347,502, filed Apr. 3, 1973, and now abandoned, from which the claims of this application have been derived.

BACKGROUND OF THE INVENTION

In an attempt to produce a new class of polyimide resins which would terminate with acetylenic groups, a search of the prior art processes for making desired acetylenic intermediates disclosed only a process for making p-aminophenylacetylene. This prior art process started with 4-nitrostyrene which in turn was reacted with bromine. The bromine reacted across the unsaturated bridge to form the α,β-dibromo ethyl group. When this compound was reacted with sodium hydroxide, the α,β-dibromo ethyl radical was converted to an acetylenic group. The nitro group was then reduced with stannous chloride in the presence of hydrochloric acid, thus forming 4-aminophenylacetylene. However, in our attempts to produce 3-aminophenylacetylene from 3-nitrostyrene by means of the same process, the desired compound was not identifiable in the reaction mixture.

BRIEF DESCRIPTION OF THE INVENTION

I have discovered that amino arylacetylenes are readily produced in good yield by reacting an aromatic compound which has both nitro and acetyl substitutents with phosphorous oxychloride in the presence of dimethylformamide to convert the acetyl group to —C(Cl)=CHCHO. This compound in turn is converted to the corresponding nitro substituted aromatic acetylene by reacting it in a solution of sodium hydroxide and dioxane, preferably under refluxing conditions. The nitro group is then reduced to the corresponding amino group by reacting it with ferrous sulfate in aqueous alcohol solution, preferably under reflux conditions.

DETAILED DESCRIPTION

I have discovered a process which is capable of making a large number of compounds. With one exception, i.e. p-aminophenylacetylene, these compounds are novel. The compounds produced by my process correspond to the following formula: $H_2N-R-C\equiv CH$ wherein R is

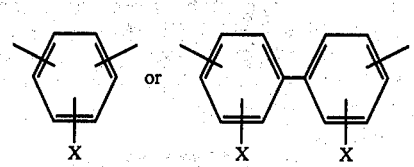

and X is hydrogen, methyl, phenyl, methoxy, fluoro or chloro. My invention includes (a) the novel process set forth below, (b) compounds of the above formula wherein R is a phenylene radical as defined above and the $NH_2$ group is in meta position to be $C\equiv CH$ group, and (c) compounds of the above formula where R is a diphenylene radical as defined above.

My process starts with compounds of the formula

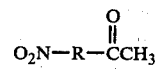

wherein R has the meaning set forth above. The nitro compound is added to a previously prepared mixture of phosphorus oxychloride in anhydrous dimethylformamide. The mol ratio of dimethylformamide and phosphorus oxychloride to the nitro compound should be at least stoichiometric. I prefer to use a considerable excess of dimethylformamide because the excess may be used as a solvent for the total mixture. A stoichiometric excess of $POCl_3$, e.g. 10 percent, helps to convert all of the acetyl groups to -C(Cl)=CHCHO. This reaction is strongly exothermic, and the temperature of the reaction should be kept at approximately room temperature, i.e. 20° to 25° C. by careful addition of the nitro compound with simultaneous application of cooling. After all the nitro compound is added, external cooling can be discontinued. The temperature will rise slightly, e.g. to approximately 55° C., after which it gradually returns to ambient temperature over a period of time, indicating completion of the reaction. The reaction mixture is then poured into a cold alkali bicarbonate solution in which sufficient bicarbonate is present to keep the pH at 7 to about 9. The resultant precipitate is removed from the liquid, preferably by filtering, and purified by conventional means, e.g. distillation or recrystallization.

The β-chloro-substituted aldehyde radical is converted to the corresponding acetylene radical by reacting the aldehyde compound in alkalinedioxane solution such as a solution of dioxane and sodium hydroxide. The reaction will proceed slowly at room temperature. For practical reasons, it is carried out at elevated temperatures. I prefer to add a dioxane solution of the aldehyde compound to a refluxing aqueous solution of sodium hydroxide at such a rate that refluxing does not stop. The ratio of sodium hydroxide to aldehyde should be at least stoichiometric; some excess hydroxide is preferred to neutralize HCl by product. Sufficient dioxane should be used to insure dissolution of all the aldehyde compound. Excess dioxane is unnecessary.

Conversion of the β-chloro aldehyde radical to the $C\equiv H$ radical is very fast, particularly when the aldehyde is added under reflux conditions. Upon completion of the reaction, 50 percent to 75 percent of the solvent is preferably removed, e.g. on a rotary evaporator, and the remaining solution is then diluted with water and chilled, preferably to 0° C. The resultant aqueous suspension is extracted with a low boiling organic solvent, such as ether, and the organic solution is dried with a desiccant, such as potassium carbonate. The dried solution is filtered, and the organic solvent is evaporated, the product is distilled under vacuum. After the solvent has been removed, the desired product is the next fraction to distill, leaving behind a small amount of residue.

The nitro group on the aromatic nucleus of the resultant acetylenic compound is reduced to the corresponding amino radical by reaction of the nitro compound in an aqueous alcohol solution of ferrous sulfate. For practical application, the reaction is carried out at elevated temperatures, and it proceeds rapidly to completion at the boiling point of the mixture. In a preferred method, I add a solution of the nitro compound in absolute ethanol to a refluxing aqueous solution of ferrous sulfate. At least 6 moles of ferrous sulfate are required per mol of nitro compound. Excess ferrous sulfate may be employed but it does not provide any noticeable results. After all the nitro compound has been added, refluxing is continued for approximately another hour to ensure complete conversion. After this, ammonium hydroxide is added to the mixture to make it alkaline.

The resultant amino compound is then extracted with an organic solvent such as ether. The organic solvent is separated from the amino compound by distillation. If there are traces of ethanol and water remaining, these may be removed under vacuum with an aspirator. The product is then purified, e.g. by recrystallization.

Having described my invention in general terms, I shall now illustrate it with typical examples.

I. m-Nitro-β-chlorocinnamaldehyde

To 400 ml of anhydrous dimethylformamide was added with stirring 455 g. (3.01 moles) of phosphorus oxychloride. The mixture was kept at 20° to 25° throughout the addition by external cooling. After standing overnight, a solution of 330 g. (2 moles) of m-nitroacetophenone in 400 ml anhydrous dimethylformamide was added dropwise, keeping the pot temperature at 20° to 25° by external cooling. Addition required about ½ hour. Stirring was continued without external cooling, during which time the temperature rose to 55° C. and then dropped to ambient temperature. The mixture was poured into cold sodium bicarbonate solution, keeping the pH at least 7, and the crude product was filtered. This product was taken up in ca. 1 liter of benzene and separated from residual water entrained by the crystals by drying with anhydrous potassium carbonate. The benzene solution was concentrated on a rotary evaporator to approximately one-third of its volume, and hexane was added until the hot solution just began to cloud. A small amount of benzene dissolved some material that oiled out, and the solution was cooled to yield crystals m.p. 83°. A second crop was obtained by evaporation of the filtrate and cooling. Total yield 195.7 g. (46.4%).

Anal. Calculated for $C_9H_6NO_3Cl$; C, 51.08; H, 2.86; N, 6.62; Cl, 16.76 Found: C, 51.20; H, 2.85; N, 6.73; Cl, 16.85

II. Base Fragmentation of m-Nitro-chlorocinnamaldehyde to m-nitrophenylacetylene To a refluxing solution of 25 g. (0.62 moles) of sodium hydroxide in 200 ml. of water in 1000 ml. flask equipped with magnetic stirrer, addition funnel, and reflux condenser, was added a solution of 53 g. (0.25 moles) of α-chloro-3-nitrocinnamaldelhyde in 300 ml. of dioxane at such a rate that refluxing did not stop. Addition required ¾ hours. After the addition was completed, refluxing was continued for an additional one-half hour. Approximately two-thirds of the solvent was removed on the rotary evaporator and the dark solution was poured into approximately 500 ml. of water containing ice cubes. The resulting aqueous suspension was extracted with ether, dried for a few minutes with potassium carbonate, and filtered. The ether filtrate was distilled over the steam bath and the residue was transferred to a small distillation setup. The product was collected at 80° (1mm.) to yield 23.17g. (63%) of m-nitrophenylacetylene, $n_D^{22}$ 1.5870.

Anal. Calculated for $C_8H_5NO_2$: C, 65.31; H, 3.43; N, 9.52 Found: C, 65.56; H, 3.51; N, 9.43. The infrared and NMR spectra were consistent with the structure.

III. Reduction of 3-nitrophenylacetylene to 3-aminophenylacetylene

To a refluxing solution of 500g (1.8 moles) of Fe-SO₄.7H₂O in 700 ml. of water was added, over a period of ¾ hour, a solution of 34.9g. (0.237 moles) of m-nitrophenylacetylene (G1325-34) in 350 ml. of absolute ethanol. The stoichiometry requires 6 moles of ferrous sulfate to reduce 1 moles of nitro compound. Refluxing was continued for an additional 2½ hours, after which 170 ml. of conc. NH₄OH was added over a period of 15 minutes. Refluxing was continued for an additional 45 minutes and the mixture was allowed to cool overnight.

An additional 100 ml. of ammonium hydroxide was added and the mixture was extracted with five portions of ether to make a total extract of 800–900 ml. The ether extract was distilled over a steam bath, with aspirator vacuum being applied at the end to remove remaining ethanol and water. The cloudy residue was taken up in 200 ml. of ether, dried over anhydrous potassium carbonate and filtered. The filtrate was distilled over the steam bath, and the residue degassed with a vacuum pump. The degassed residue was carefully transferred to a Hickmann molecular still, further degassed, and distilled at a pressure of 100 μ, using gentle heat from a heat gun. The fluid temperature remained below ca. 50° C. during the distillation. A yield of 24.6 g. (89%) was obtained, $n_D^{22}$ 1.6173. The presence of amino and acetylene groups was clearly shown by both IR and NMR spectroscopy. Titation with a standard solution of perchloric acid in glacial acetic acid gave an equivalent weight of 118.1 (Cald. 117).

Anal. Calculated for $C_8H_7N$; C, 82.02; H, 6.02; N, 11.96; M.W. 117 Found: C, 81.86; H, 6.08; N, 12.04; M.W. (by vapor osometry in benzene) 125

I claim:

1. A process for making a compound of the following formula:

$$O_2N-R-C \equiv H$$

which comprises reacting in alkaline-dioxane solution a compound of the formula:

$$O_2N-R-C=CHCHO$$
$$|$$
$$Cl$$

R being

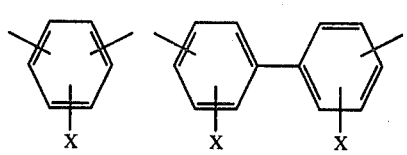

and X is hydrogen, methyl, phenyl, methoxy, fluoro or chloro.

2. A process of claim 1 wherein said alkalinedioxane solution is maintained under reflux conditions.

3. A process of claim 2 wherein the nitro compound reactant is m-nitro-β-chlorocinnamaldehyde.

4. A process for making an aldehyde compound of the following formula:

$$O_2N-R-C=CHCHO$$
$$\quad\quad\quad\quad |$$
$$\quad\quad\quad\quad Cl$$

which comprises contacting a compound of the following formula:

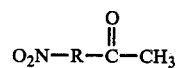

R being

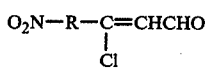

and X is hydrogen, methyl, phenyl, methoxy, fluoro or chloro, with a solution of POCl$_3$ and dimethyl formamide to form corresponding aldehyde compound, pouring resultant solution into cold alkali bicarbonate while keeping pH of resultant mixture from 7 to about 9, and recovering precipitated aldehyde compound.

5. A process of claim 4 wherein R is phenyl, NO$_2$ is meta or para to

and the alkali bicarbonate is sodium bicarbonate.

* * * * *